United States Patent [19]

Thornton

[11] Patent Number: 5,036,856

[45] Date of Patent: Aug. 6, 1991

[54] CARDIOVASCULAR MONITORING SYSTEM

[76] Inventor: William E. Thornton, 701 Coward's Creek Rd., Friendswood, Tex. 77546

[21] Appl. No.: 554,421

[22] Filed: Jul. 19, 1990

[51] Int. Cl.⁵ ............................................. A61B 5/02
[52] U.S. Cl. .................................. 128/670; 128/710; 128/782
[58] Field of Search ............... 128/670, 710, 782, 668, 128/903, 671

[56] References Cited

U.S. PATENT DOCUMENTS

| | | | |
|---|---|---|---|
| 3,548,806 | 12/1970 | Fisher | 128/671 |
| 3,675,640 | 7/1972 | Gatts | 128/671 |
| 3,894,533 | 7/1975 | Cannon | 128/671 |
| 4,483,346 | 11/1984 | Slavin | 128/710 |
| 4,803,996 | 2/1989 | Peel et al. | 128/710 |
| 4,827,943 | 5/1989 | Bornn et al. | 128/903 |
| 4,830,021 | 5/1989 | Thornton | 128/782 |
| 4,883,063 | 11/1989 | Bernard et al. | 128/670 |

Primary Examiner—Francis Jaworski
Assistant Examiner—George Manuel

[57] ABSTRACT

A cardiovascular monitoring system which generates signals representative of certain physical activities of the subject and additional signals representing the emotional state of the subject in conjunction with the usual EKG signals. All of the signals generated by the monitoring system are digitized and multiplexed so that the signals representing the physical activities and emotion states of the subject may be recorded in a single channel. A usual Holter recorder may be used for recording the EKG signals, and the additional signals may be recorded in a separate recorder, or in a separate channel on the Holter recorder. The additional signals may be correlated with the EKG signals for the examination of the physical activities and emotional states of the subject which could cause detected abnormalities in the EKG signals.

11 Claims, 7 Drawing Sheets

CARDIOVASCULAR MONITORING SYSTEM

BACKGROUND OF THE INVENTION

Continuous, twenty-four hour or longer, electrocardiogram (EKG) monitoring (Holter) systems are widely used in the prior art for diagnosing heart disease. However, the long term prior art EKG monitoring systems are concerned only with EKG signals which is one of their shortcomings.

There is another much simpler diagnostic means used in the prior art, namely the brief exercise "stress test" in which the EKG is recorded during a brief time interval while the patient is exercising strenuously on a treadmill. However this latter test is not comprehensive because exercise is only one of a number of stresses that can cause EKG abnormalities.

U.S. Pat. No. 4,830,021 which issued May 16, 1989 to the present inventor describes a locomotor activity monitoring system which involves EKG and which involves long term monitoring of the patient. The system described in that patent, unlike other prior art cardiac monitoring systems, uses EKG only incidentally and primarily to monitor heart rate.

There are shortcomings in each of the prior art systems referred to above. For example, the Holter system has no detection/recording capability other than time, EKG readings and a patient marker. The patient maintains a time related diary of such events. At best this approach is qualitative. It is also incomplete, since no data is entered, for example when the patient is asleep. In essence, there is no objective or recorded evidence of any patient activity.

The cardiac abnormalities which are revealed by the prior art cardiac monitoring systems are equated only to physical activities. However, such cardiac abnormalities may also be revealed by a number of other conditions in the boy. Knowledge of these conditions, other than physical activity, which provoke detectable cardiac abnormalities is frequently important for determining the proper treatment. As noted above, such knowledge cannot be acquired from current cardiac monitoring systems and techniques. Copending application Ser. No. 554,549, filed July 19, 1990, in the name of the present inventor discloses a cardiac monitoring system which in addition to physical activities also monitors such other conditions in the body.

Specifically, the system disclosed in the Copending Application, in addition to collecting ambulatory data such as described in U.S. Pat. No. 4,830,021 also collects additional data relating to activities which also affect or define cardiac responses of the subject. Such additional activities may include, for example, verbal exchanges, evidence of emotional stress arising from verbal exchanges between the subject and others, emotional stress arising from dreams, and other physical conditions such as the posture of the subject, air temperature, ambient light level, elapsed time, and so on.

It is well known, for example, that inadequate blood supply to the heart may alter a portion of the EKG known as the S.T. segment. It is also well known that the most common cause of inadequate blood supply to the heart is partial closure of one or more arteries by fatty formations. Limited blood flow through a narrowed artery which is inadequate to meet the needs demanded by exercise is the most common cause of such EKG changes. However, normal or slightly affected arteries may produce the same effect due to spasms from emotional upsets which are transmitted to the heart by the nervous system, and which are not detected by the prior art cardiac monitoring systems. The treatment in the case of clogged arteries is normally surgery, but a vastly different treatment is required in the case of arterial spasm caused, for example, by emotional upsets in relatively normal arteries, or even in arteries which are partially occluded.

For example, external events known to cause cardiovascular problems include: physical stress; work; exercise; temperature extremes and changes; and fatigue. In addition, there are emotional stresses which also can cause cardiovascular problems, and these include, for example, such emotional stresses as real or perceived danger, anger, conflict, and the like; which may be provoked by the environment, or which may arise during certain phases of sleep.

One objective of the present invention is to provide a relatively simple and practical system which detects and records parameters affecting the cardiovascular system of a subject simultaneously with the recording of the EKG data. On replay, should EKG abnormalities be detected in the operation of the system of the invention, the record can be correlated and examined for physical and emotional activities and environmental parameters which could cause such abnormalities.

In accordance with the present invention, a prior art four-channel Holter magnetic tape recorder may be provided, three channels of which may be used to record EKG signals, and the fourth channel used to record time signals and additional patient data in multiplexed digital and other encoded form. This additional patient data may then be stored/analyzed in a digital computer which correlates the data and produces a report which contains, for example, a summary of the EKG data such as heart rate, S.T. level, plots of the data, examples of abnormal EKG activity, and potential diagnosis based on the data. By adding data related to physical and emotional stresses in accordance with the present invention, the specificity and the reliability of the diagnosis and treatment can be increased.

The system of the invention also has the ability of cross correlation of environmental data or enhance its ability and reliability in the detection of specific events and correlation of EKG events and external events to improve diagnosis.

SUMMARY OF THE INVENTION

The invention provides a cardiovascular monitoring system which monitors not only the EKG of a subject, but also certain physical activities and emotional states of the subject and environmental data. The system includes in addition to the EKG sensors, additional sensors which are affixed to the subject and which generate additional signals indicative of certain physical activities being carried out by the subject and also of the emotional state of the subject. These additional signals are digitized and multiplexed and recorded along with the EKG signals, either on the same recorder or on a separate recorder and are used in the examination of the physical activities and emotional states of the subject which could have caused detected abnormalities in the EKG signals.

DETAILED DESCRIPTION OF THE ILLUSTRATED EMBODIMENT

Figure 1:
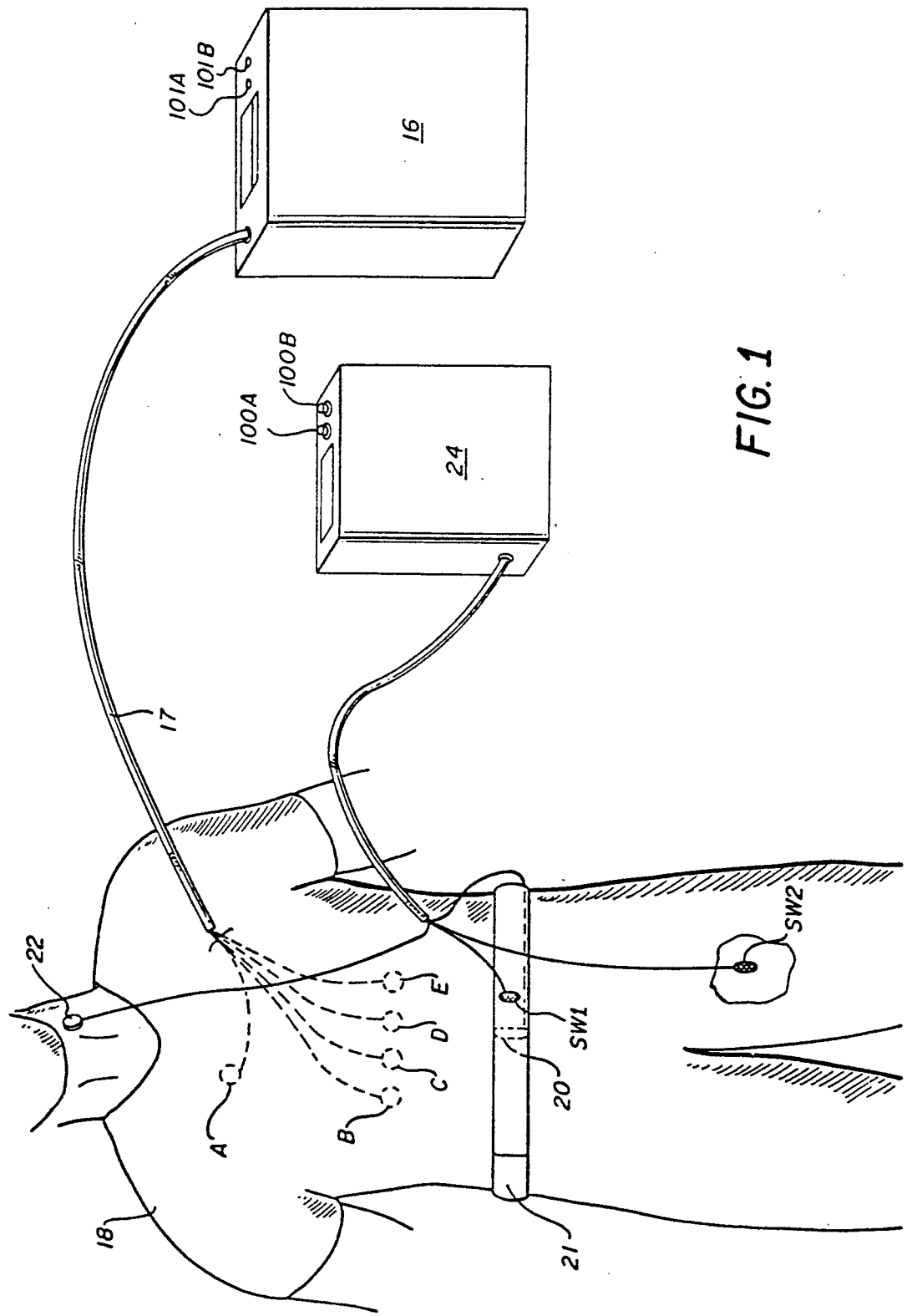
FIG. 1 is a representation of a subject on which various sensors and other instruments are mounted for carrying out desired cardiac monitoring functions.

In order for the Augmented Holter Monitoring (AHM) system of the invention to perform its desired monitoring functions, it is necessary for the subject 18 of FIG. 1 to carry certain sensors, transducers and other equipment as described in the Copending Application. For example, the subject 18 may carry an existing miniature EKG Holter recorder 16 in one of his shirt pockets. Usual EKG electrodes A-E are mounted on the subject and connected to the Holter recorder 16 over leads 17. The subject 18 also carries a miniature accelerometer 20 on a belt 21, the accelerometer measuring vertical accelerations (Gz) of the subject at his center of gravity. The accelerations (Gz) are converted to vertical forces (Fz) by the system in a manner fully described in U.S. Pat. No. 4,830,021.

Two position sensor switches SW1 and SW2 are also attached to subject 18, one at his waist and the other on his thigh. Switches SW1 and SW2 may be commercially available mercury gravity switches, or other appropriate gravity switches may be used. These switches serve to provide indications of the posture of the subject, specifically whether the subject is standing, sitting or lying down. The operation of such switches is described in some detail in U.S. Pat. No. 4,830,021.

A multiple sensor 22 is mounted on the neck of subject 18. This multiple sensor may include two microphones, as will be described, as well as light and temperature sensors. The light sensor may be a simple photodiode circuit which generates electrical signals indicative of ambient light levels. The temperature sensor may be a thermistor circuit which generates electrical signals indicative of ambient temperature. The sensors 20, SW1, SW2 and 22 are all connected to a second recorder 27 which may fit into a second shirt pocket of subject 18, or which may be clipped to the Holter recorder 16. Alternately, recorder 24 may be combined in Holter recorder 16.

Figure 2B:
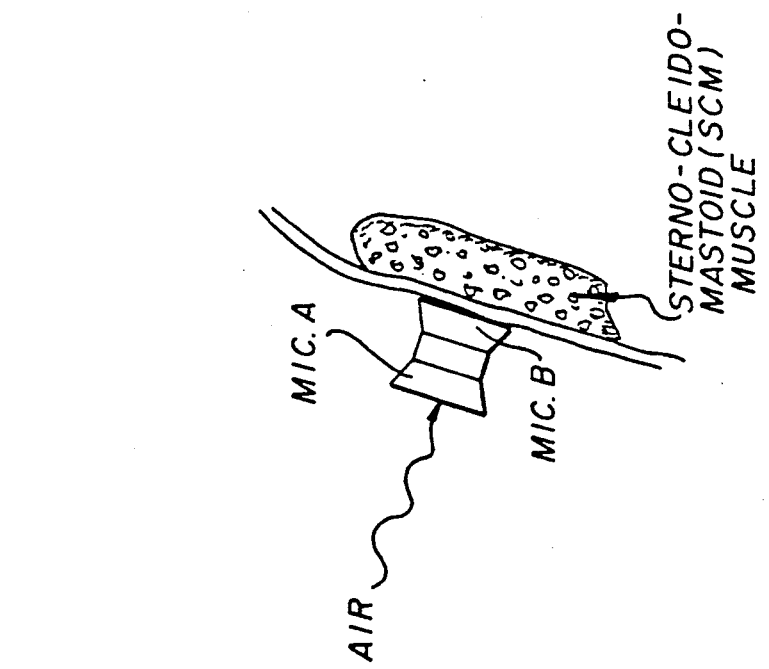
FIG. 2A and 2B constitute a further representation of the subject shown in FIG. 1, and show the manner in which first and second microphones are mounted on the subject for purposes to be explained, FIG. 2B being a section taken along the line 2B—2B of FIG. 2A.
Figure 2A:
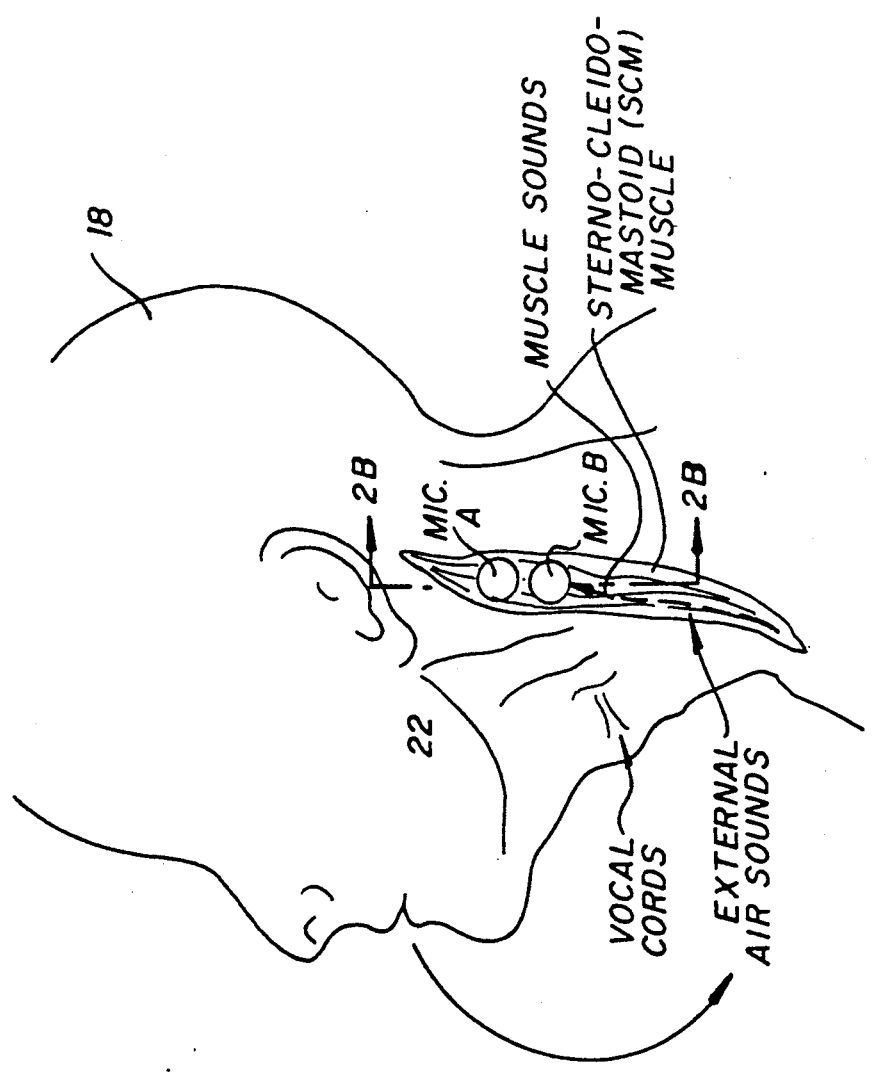

As shown in FIGS. 2A and 2B, multiple sensor 22 includes two microphones designated Mic "A" and Mic "B". Microphones Mic "A" and Mic "B" may be subminiature microphones of the dynamic, electrode or semiconductor type, and preferably have frequency responses in the range of 20–3000 Hz. Microphone Mic "B" is attached to the neck of subject 18 adjacent to the sterno-cleido-mastoid (SCM) muscle above the collar. Microphone Mic "B" registers strong vibrations from the voice of subject 18 (0.3–3 KHz); weaker vibrations from external sources including voices (0.3–3 KHz); and lower frequency vibrations due to muscle contractions of the subject occurring, for example, when the subject is asleep and is experiencing an emotional dream. Microphone Mic "B" should have a high/low frequency response at approximately 10 Hz to respond to the low frequency (16 Hz) of muscle activity.

Although the microphones Mic "A" and Mic "B" are shown displaced from one another in FIG. 2A, microphone Mic "A", is pr4eferably mounted on microphone Mic "B" as shown in FIG. 2B, and the microphones are acoustically isolated from one another. Microphone Mic "A" serves to register the speech of the subject as transmitted through air, and it also registers other sounds transmitted to it by air.

Figure 3:
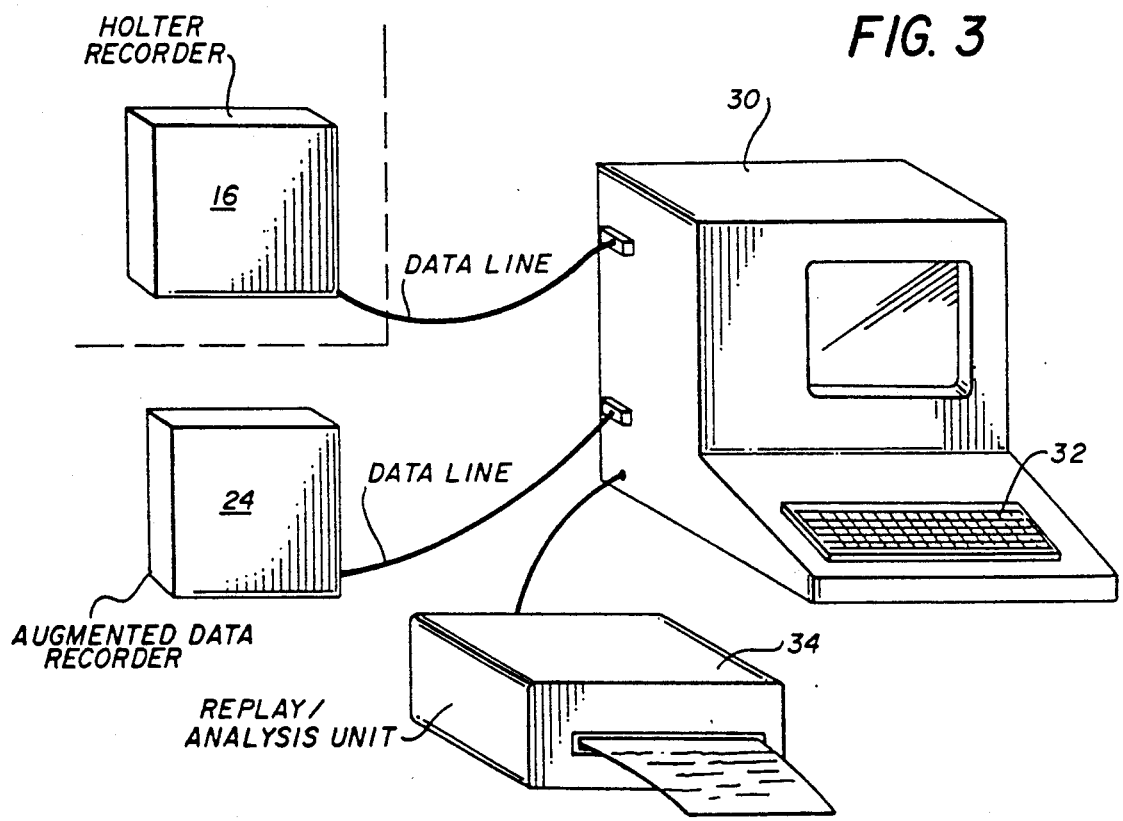
FIG. 3 is a block diagram of a Holter replay/analysis unit which is used to receive data from recorders carried by the subject of FIG. 1.

A conventional Holter replay/analysis unit 30 is shown in FIG. 3. The recorders 16 and 24 of FIG. 1 are connected to unit 30 during replay, as shown, and data recorded on recorders 16 and 24 is fed into the unit. Unit 30 includes all usual components, including a computer, controls, displays, a keyboard 32 and a printer 34, all of which are needed for processing, and displaying the augmented Holter data from recorders 16 and 24. The augmented Holter data from the recorders (which must be time tagged) is digitized and stored in unit 30.

The vertical acceleration (Gz) outputs of accelerometer 20 of FIG. 1, which represents the locomotor activity of the subject, has a characteristic waveform which varies synchronously both in frequency and amplitude with the step frequency of the subject. The locomotor activity is such that a sample rate of one per minute, that is, the number of steps and mean force developed, is adequate. A circuit for achieving the foregoing would normally be incorporated into recorder 24. Such a circuit is shown in the block diagram of FIG. 4.

Figure 4:
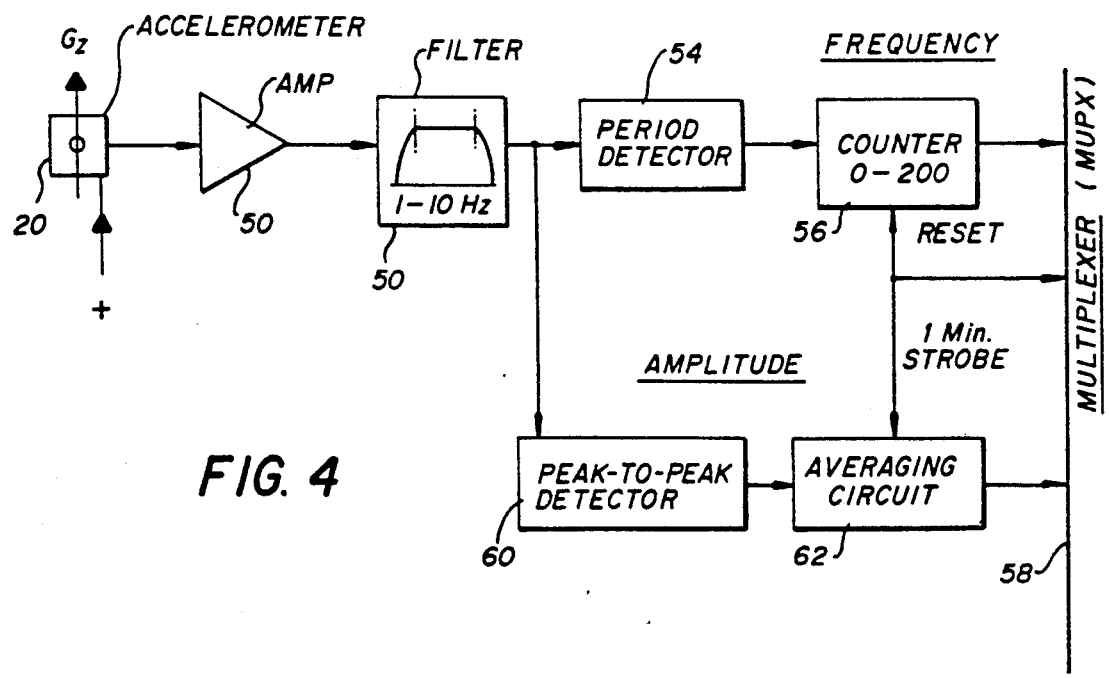
FIG. 4 is a block diagram of the manner in which vertical acceleration signals of the subject are processed.

In FIG. 4, accelerometer 20 is connected to an amplifier 50 which, in turn, is connected through a bandpass filter 52 to a period detector 54. The period detector 54 is connected to a counter 56 for detecting the frequency of the waveform. The output of counter 56 is connected to a bus 58 which carries the signals from the counter to an appropriate multiplexer (MUPX). Filter 52 is also connected to a peak-to-peak detector 60 for detecting the amplitude of the waveform. The output of peak-to-peak detector 60 is connected to an averaging circuit 62 whose output is also connected to bus 58. Counter 56 and integrator circuit 62 are each reset by an appropriate one minute strobe, as shown. The multiplexer MUPX causes the data from the circuit of FIG. 4 to be recorded in recorder 24, multiplexed with other data from the sensors of FIG. 1. All of the data is preferably recorded in digital form.

Figure 5:
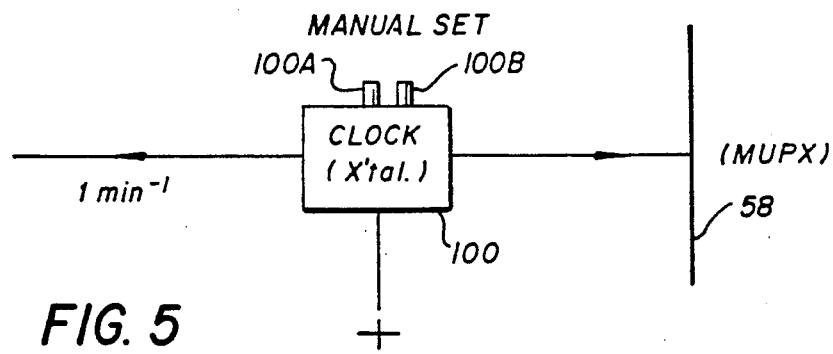
FIG. 5 is a block diagram of a master digital clock which is included in the recorders forming a part of the system.

A crystal time clock 100, as shown in FIG. 5, is included in recorder 24. The time clock may include the usual manual set controls 100A, 100B which are also shown in FIG. 1. Discrete twenty-four hour time signals and a 1 min-1 code is generated by the clock 100. The discrete time signals are introduced to bus 58 which carries the signals to the multiplexer MUPX to be recorded in digital form in recorder 24 multiplexed with the other digital data. A similar time clock may be included in recorder 16 (FIG. 1) with manual time set controls 101A and 101B. Such a clock would provide all time signals in a single unit recorder.

Figure 6:
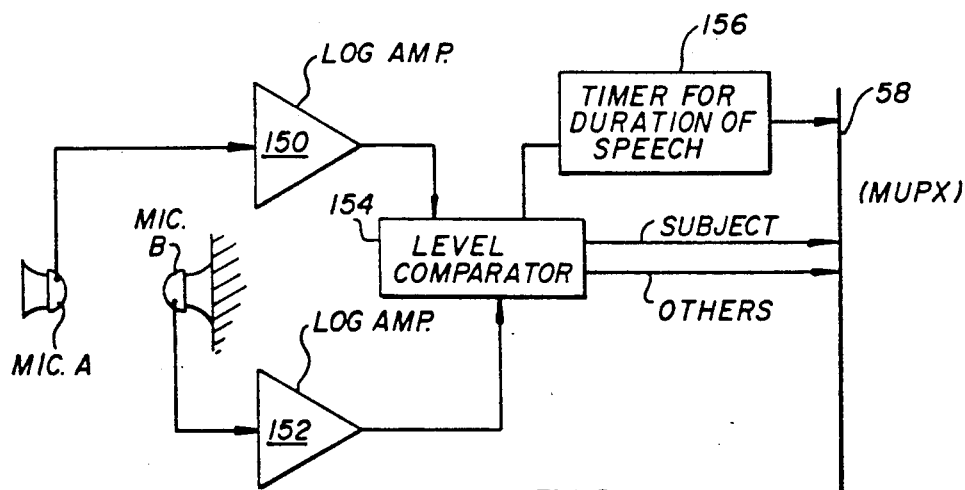
FIG. 6 is a block diagram showing the manner in which signals representing the speech of the subject and others are processed in the system.
Figure 7:
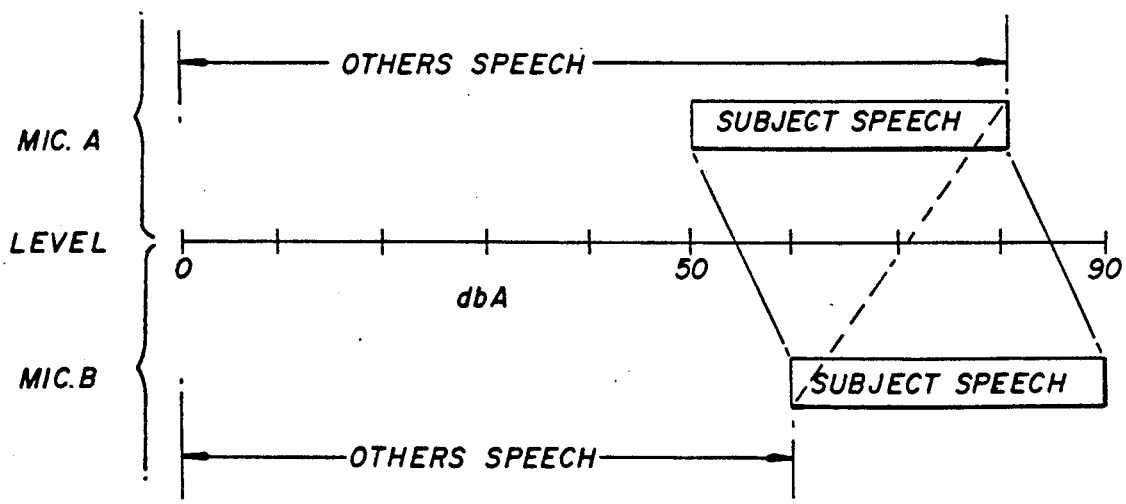
FIG. 7 is a schematic representation of the incidence of speech by the subject and by others monitored by the system.

The outputs from microphones Mic "A" and Mic "B" of FIGS. 2A and 2B are amplified by respective log amplifiers 150 and 152 in the circuit of FIG. 6, which circuit is included in recorder 24. The amplified outputs from the log amplifiers are compared in a level comparator 154 for amplitude differences. The comparator 154 provides output signals which distinguish the subject's speech from the speech of others, and such signals are applied to bus 58 to be carried to multiplexer MUPX and to be recorded in recorder 24 in digital form. The circuit of FIG. 6 also includes a timer 156 which provides time signals for timing the duration of speech components of the subject and of others. The speech of the subject and the speech of others may be distinguished because of amplitude differences, as shown in the representation of FIG. 7.

Figure 8:
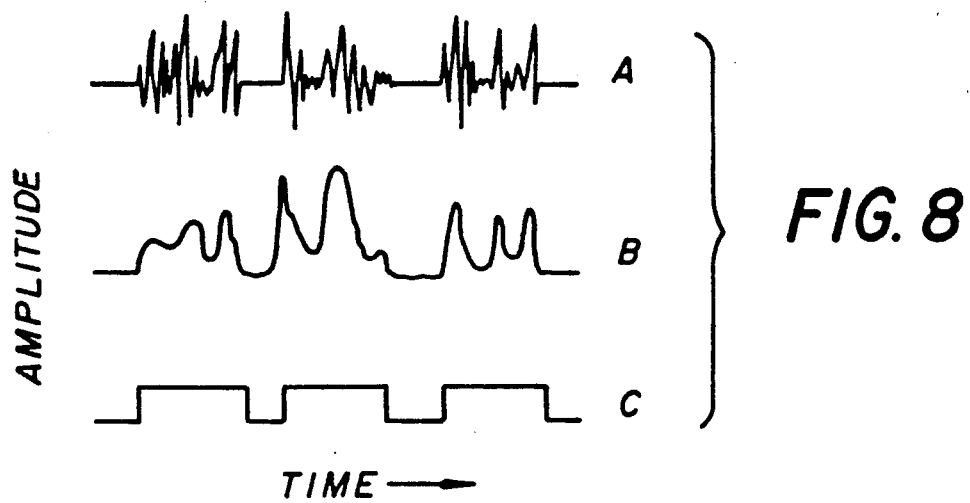
FIG. 8 is a series of curves representing the voice pattern of the subject of FIG. 1 during normal conditions.
Figure 9:
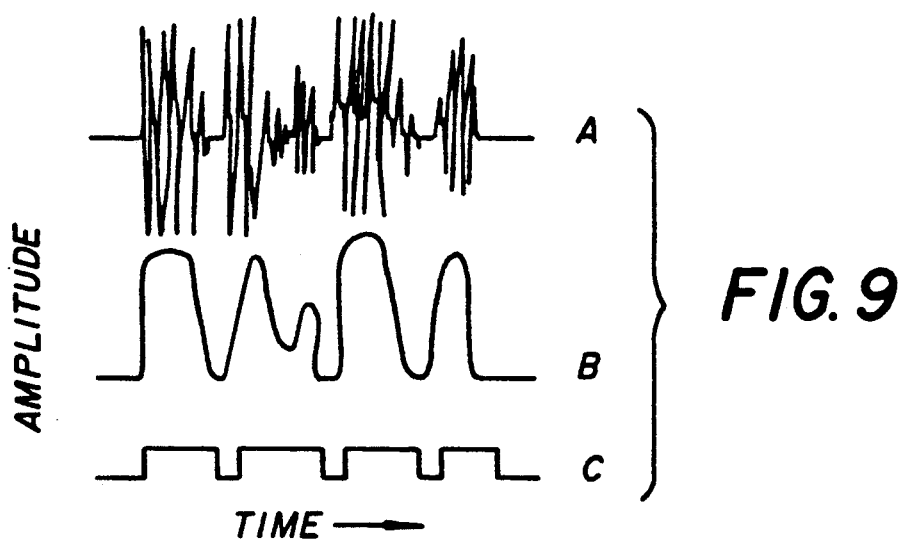
FIG. 9 is a series of curves showing the voice pattern of the subject of FIG. 1 during emotional conditions.

The normal voice of the subject 18, when not under emotional stress, is represented by curves A, B and C in FIG. 8; and the voice of the subject when under emotional stress is represented by the curves of FIG. 9. The speech of the subject and its emotional content is detected by the duty cycle of the sound envelopes, and this is achieved by comparing the ratios of the on and off times of the speech of the subject. That is, as the subject becomes emotional there will be less space between the words and the words will be shorter. It is also desirable to include an amplitude detector, since a raised voice is also a usual concomitant of emotion.

Figure 10:
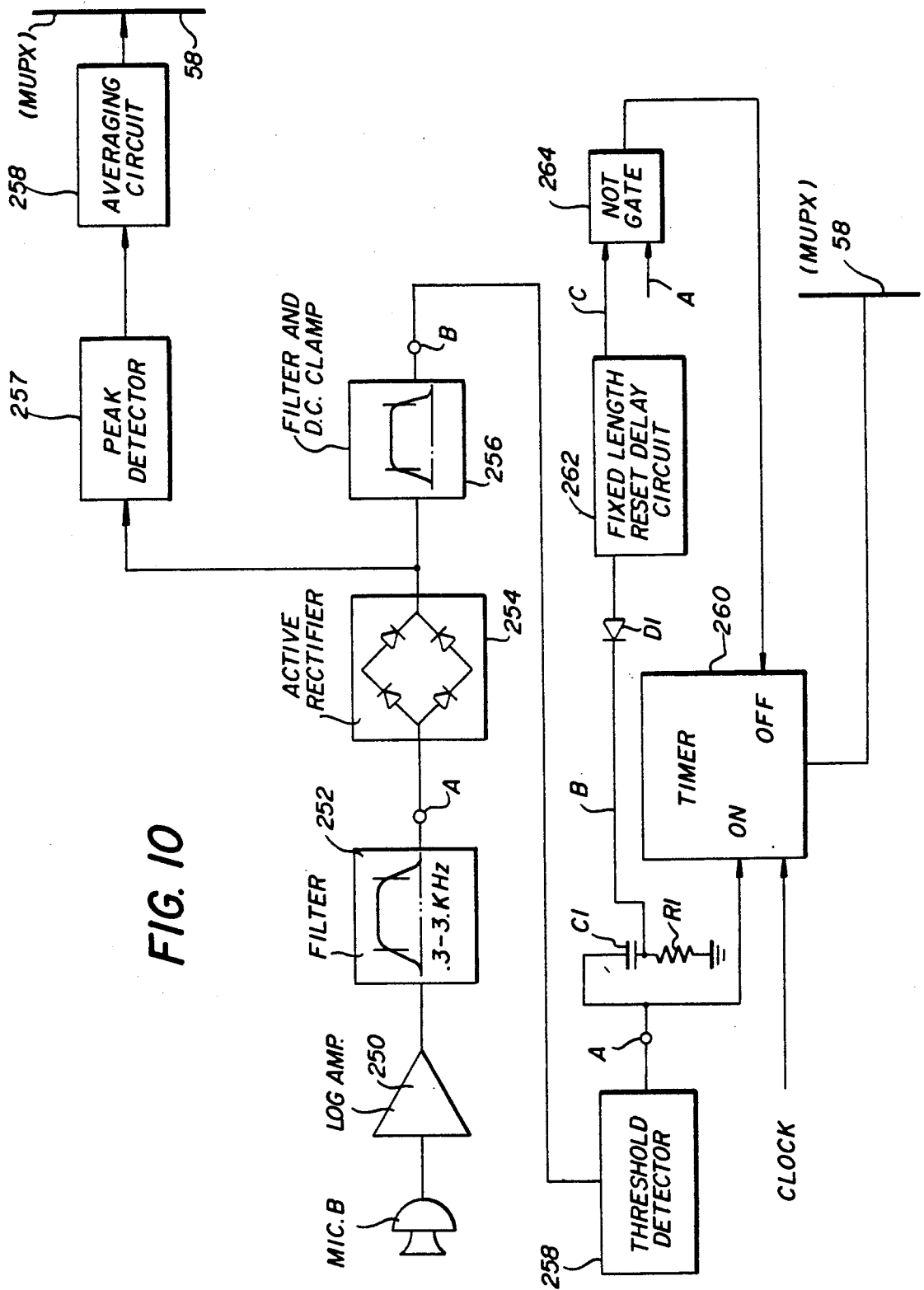
FIG. 10 is a block diagram of a circuit which responds to the voice pattern of the subject to determine the emotional state of the subject.

A circuit for detecting the emotional content of the speech of the subject is included in recorder 24, and a typical circuit is shown in block diagram in FIG. 10. In FIG. 10, the microphone Mic "B" is connected to a log amplifier 250 which, in turn, is connected through a bandpass filter 52 to a precision active rectifier 254. The output of rectifier 254 is passed through a filter and DC clamp circuit 256 to a threshold detector 258. The threshold detector is connected the "on" input of a timer 260 which measures the on and off time of the speech.

The off time must be limited after an "on" cycle, otherwise it will count long periods, for example, between sentences.

Such limitation is achieved by a fixed length delay circuit 262 and a "not" gate 264./ The output of the "not" gate is connected to the "off" input of timer 260. The output of threshold detector 258 is also applied to a differentiating circuit C1, R1, which is connected to delay circuit 262 through a diode D1.

Figure 10A:
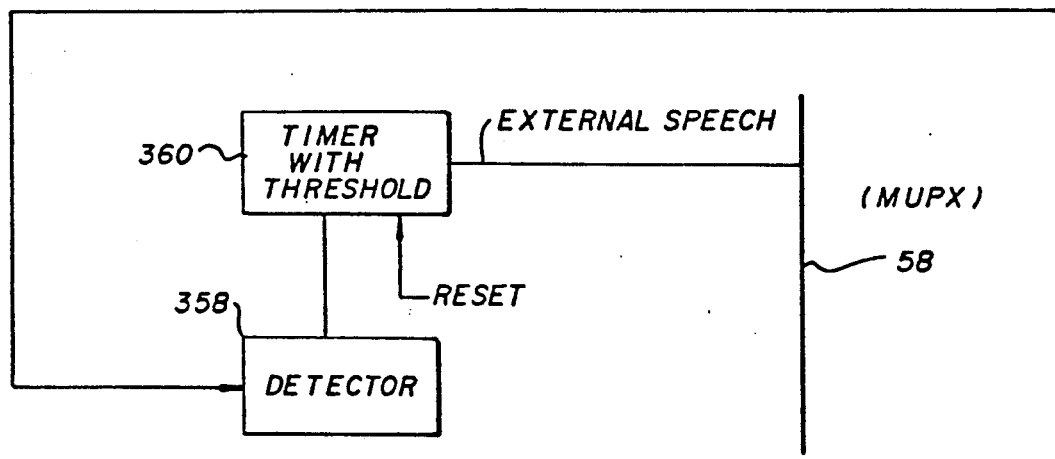
FIG. 10A shows a series of curves useful in explaining the operation of the circuit of FIG. 10.
Figure 10A:
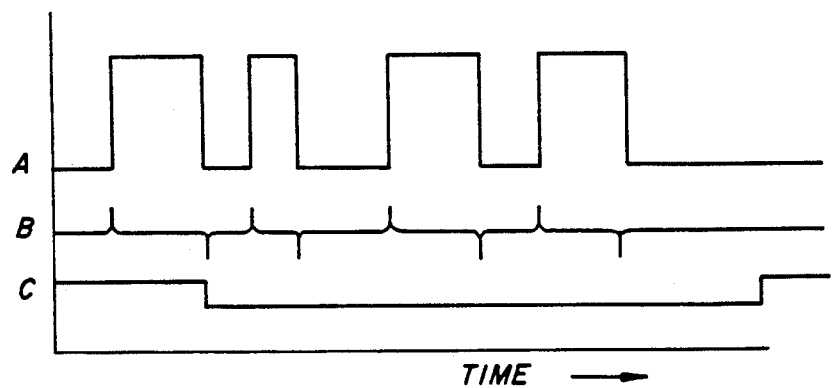

Curves A, B and C of FIG. 10A represent the waveform of the various signals in the circuit of FIG. 10. Curve A is the on/off signal, which is differentiated by the differentiator C1, R1 to generate a negative-going trigger (curve B) each time signal A goes negative. Trigger signal B triggers delay circuit 262 at time intervals longer than the usual delay between words. Delay circuit 262 is reset by each negative trigger B, and when it is not reset, its output C is high.

Timer 260 is turned on whenever signal A is low, and it is turned off whenever signal A is low. Should signal A remain low after a predetermined time interval established by delay circuit 262, it is turned off by trigger C going high while signal A is low by virtue of "not" gate 264.

As shown, the normal voice and emotional voice of the subject appears at the output of filter 252, as represented by the curve A in each of the diagrams of FIGS. 8 and 9. The rectified waveforms B of FIGS. 8 and 9 appears at the output of the filter and clamp circuit 256 in FIG. 10, and that output is transformed into a series of pulses by threshold detector 258, the pulses being shown by curves C in FIGS. 8 and 9. The closer the pulses in the curves C are together, and the shorter the pulses, the more emotional is the speech of subject 18. Pulses from the threshold detector 258 are applied to the timers 260 and 262, and a reading of the on time and off time of each of the pulses is fed to the multiplexer over bus 58 to be recorded in recorder 24.

The circuit of FIG. 10 also includes a peak detector 257 and an averaging circuit 258, which serve as an amplitude detector, for the reasons stated above.

Figure 11:
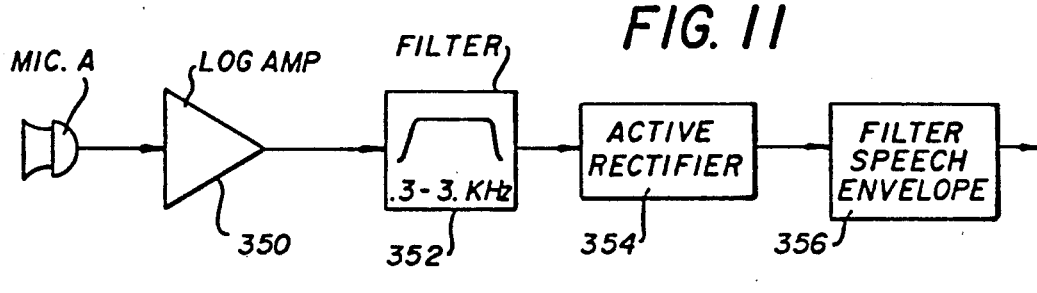
FIG. 11 is a block diagram of a circuit for detecting the incidence of speech from others apart from the subject and also for detecting ambient noise.

As mentioned above, the speech of others and external noise is detected by microphone Mic "A", and is processed by the circuit of FIG. 11. Microphone Mic "A" is connected to a log amplifier 350 which, in turn, is connected through a bandpass filter 352 to an active rectifier 354. The output of the active rectifier is passed through a filter 356 whose out put, in turn, is passed to a detector 358. Output of detector 358 is connected to a timer 360 whose output, in turn, is fed to the multiplexer MUPX over bus 58.

The circuit of FIG. 11 provides an output representative of the presence of the speech of others, and the emotional content of the speech. Noise is determined by the presence of a continuous background which results in an output from microphone Mic "A" which is of greater amplitude than the output of microphone Mic "B".

As mentioned above, the multiple sensor 22 of FIG. 1 which is mounted on the neck of subject 18 also contains a simple photodiode which is encoded into several light levels so that signals representing ambient light levels may be applied to bus 58 and transmitted to multiplexer MUPX. As also mentioned, temperature readings are provided by including a thermistor in sensor 22 and by applying its output to bus 58. The posture of the subject is also detected by applying signals from the posture sensors SW1 and SW2 of FIG. 1 to bus 58, and utilizing the signals in the manner described in U.S. Pat. No. 4,830,021.

In the foregoing manner, all of the augmented data from sensors 20, SW1, SW2 and 22 in FIG. 1 is multiplexed and recorded in digital form on recorder 24. Accordingly, the data collected by the system described above includes physical activity which requires increased heart work. The largest load in the usual subject is walking-jogging-running (locomotor activity). The monitoring of such activity is described in U.S. Pat. No. 4,830,021 which discloses a system by which such activity may be accurately detected and recorded.

In addition to physical activity, the monitoring system of the invention serves to detect and record emotional events. These emotional events are detected and recorded in the system of the invention directly, rather than relying on questionable and variable data such as galvanic skin response, as is sometimes used in the prior art. Two events known to be frequently associated with emotional stress are recorded, as described, and these comprise the presence of subject's speech and conversation, as well as dream states. The voice patterns are analyzed for emotional indicators.

Other conditions known either to effect cardiac activity or which may define cardiac activities are also recorded, and these include subject posture, that is lying, sitting, standing; as well as ambient conditions such as air temperature and ambient light level.

The invention provides, therefore, an improved cardiovascular monitoring system which detects the emotional state of a subject, and which generates signals indicative of the emotional states together with signals indicative of certain physical activities of the subject. The monitoring system records these signals, together with the EKG signals of the subject to enable an examination to be made of the physical activities and emotional states of the subject which could cause detected abnormalities in the EKG signals.

It will be appreciated that while a particular embodiment of the invention has been shown and described, modifications may be made. It is intended in the claims to cover all modifications which come within the true spirit and scope of the invention.

I claim:

1. A cardiovascular monitoring system including: first sensor means adapted to be affixed to a subject for generating EKG signals related to the subject; second sensor means adapted to be affixed to the subject; for generating signals related to certain physical activities of the subject; third sensor means adapted to be affixed to the subject for generating signals of skeletal muscle vibrations related to the source of emotional state of the subject; and recording means connected to said first, second and third sensor means for recording the signals generated thereby so that the signals generated by said second and third sensor means may be correlated with the EKG signals generated by said first sensor means to enable abnormalities in the EKG of the subject to be detected and correlated with the physical activities and emotional state of the subject.

2. The monitoring system defined in claim 1, in which said recording means includes a Holter electromagnetic recorder connected to said first sensor means for recording said EKG signals, and a separate electromagnetic recorder connected to said second and third sensor means for recording the signals generated thereby.

3. The monitoring system defined in claim 1, and which includes a fourth sensor means adapted to be affixed to the subject for generating signals related to selected ambient conditions, and means connecting said fourth sensor means to said recording means to enable signals from said fourth sensor means to be recorded thereby.

4. The monitoring system defined in claim 1, and which includes circuit means included in said recording means for multiplexing the signals from said second and third sensor means for recording in a single channel in said recording means.

5. The monitoring system defined in claim 4, in which said circuit means includes means for digitizing the signals from said second and third sensor means.

6. The monitoring system defined in claim 1, and which includes a clock circuit included in said recording means for generating time signals to be recorded in said single channel multiplexed with the signals from said second and third sensor means.

7. The monitoring system defined in claim 6, and which includes digitizing circuitry in said recording means for digitizing said time signals.

8. The monitoring system defined in claim 1, in which said third sensor means includes transducer means for detecting voice signals, and in which said recording means includes circuitry for distinguishing the speech of the subject from the speech of others and for detecting the emotional content of the speech of the subject and the emotional content of the speech of others.

9. The monitoring system defined in claim 3, and which includes fifth sensor means adapted to be affixed to the subject for generating signals related to the posture of the subject, and means connecting said fifth sensor means to said recording means for enabling signals generated by said fifth sensor means to be recorded thereby.

10. The monitoring system defined in claim 9, and which includes sixth sensor means adapted to be affixed to the subject for generating signals related to muscle contractions of the subject which occur when the subject is asleep and experiencing an emotional dream, and means connecting said sixth sensor means to said recording means to enable the signals generated by said sixth sensor means to be recorded thereby.

11. The monitoring system defined in claim 1, and which includes sensor means for generating signals related to ambient temperature and light.

* * * * *